(12) United States Patent
Cronin et al.

(10) Patent No.: US 10,595,726 B2
(45) Date of Patent: Mar. 24, 2020

(54) WEARABLE AND DETACHABLE HEALTH PARAMETER SENSOR

(71) Applicant: KONINKLIJKE PHILIPS N.V., Eindhoven (NL)

(72) Inventors: John Cronin, Bonita Springs, FL (US); Steven Philbin, Bonita Springs, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 254 days.

(21) Appl. No.: 15/556,314

(22) PCT Filed: Mar. 9, 2016

(86) PCT No.: PCT/EP2016/054949
§ 371 (c)(1),
(2) Date: Sep. 7, 2017

(87) PCT Pub. No.: WO2016/142392
PCT Pub. Date: Sep. 15, 2016

(65) Prior Publication Data
US 2018/0070824 A1   Mar. 15, 2018

Related U.S. Application Data

(60) Provisional application No. 62/130,134, filed on Mar. 9, 2015.

(30) Foreign Application Priority Data

Jul. 16, 2015   (EP) .................................... 15177049

(51) Int. Cl.
*A61B 5/00*   (2006.01)
*A61B 5/0205*   (2006.01)
(Continued)

(52) U.S. Cl.
CPC ............. *A61B 5/0022* (2013.01); *A61B 5/01* (2013.01); *A61B 5/0205* (2013.01);
(Continued)

(58) Field of Classification Search
CPC ............. A61B 5/6898; A61B 5/02055; A61B 5/02125; A61B 5/02438; A61B 5/02416;
(Continued)

(56) References Cited

U.S. PATENT DOCUMENTS

2011/0046519 A1\* 2/2011 Raheman ............... A61B 5/112
  600/595
2014/0051941 A1\* 2/2014 Messerschmidt .... A61B 5/6898
  600/301

FOREIGN PATENT DOCUMENTS

| WO | WO2013066642 A1 | 5/2013 |
| WO | WO2014028736 A1 | 2/2014 |
| WO | WO2015031278 A1 | 3/2015 |

OTHER PUBLICATIONS

Letter and Amendment in Response to the International Search Report and the Written Opinion of the International Searching Authority Under Article 34, David Rodack, dated Dec. 1, 2016.
(Continued)

*Primary Examiner* — Eric F Winakur
*Assistant Examiner* — Chu Chuan Liu

(57) ABSTRACT

In one embodiment, a system (200) comprising a wearable base (104) and a detachable health-parameter sensor apparatus (108) detachably coupled to the base, the detachable health-parameter sensor apparatus automatically and repeatedly monitoring one or more health parameters of a user, and responsive to determining a need for truer readings, instructing the user to locate the health-parameter sensor apparatus to another location on the user.

17 Claims, 11 Drawing Sheets

(51) Int. Cl.
  *G06F 19/00* (2018.01)
  *A61B 5/01* (2006.01)
  *A61B 5/026* (2006.01)
  *A61B 5/08* (2006.01)
  *A61B 5/145* (2006.01)
  *G16H 40/63* (2018.01)

(52) U.S. Cl.
  CPC ........ *A61B 5/02055* (2013.01); *A61B 5/0261* (2013.01); *A61B 5/0816* (2013.01); *A61B 5/14532* (2013.01); *A61B 5/681* (2013.01); *A61B 5/6802* (2013.01); *A61B 5/6814* (2013.01); *A61B 5/6815* (2013.01); *A61B 5/6823* (2013.01); *A61B 5/6831* (2013.01); *A61B 5/742* (2013.01); *A61B 5/7455* (2013.01); *A61B 5/7465* (2013.01); *A61B 5/7475* (2013.01); *G06F 19/3418* (2013.01); *G16H 40/63* (2018.01); *A61B 2560/0412* (2013.01); *A61B 2560/0443* (2013.01); *A61B 2562/0204* (2013.01); *A61B 2562/0219* (2013.01)

(58) Field of Classification Search
  CPC ... A61B 5/0404; A61B 5/0533; A61B 5/0537; A61B 5/0022; A61B 5/681; A61B 5/0261; A61B 5/0816; A61B 5/01; A61B 5/742; A61B 5/7455; A61B 5/7465; A61B 5/7475; A61B 5/6814; A61B 5/1455; A61B 5/14551; A61B 5/14532; A61B 5/6802; A61B 5/6815; A61B 5/6823; A61B 5/6831
  See application file for complete search history.

(56) References Cited

OTHER PUBLICATIONS

PCT International Search Report, International application No. PCT/EP2016/054949, dated Mar. 9, 2016.

\* cited by examiner

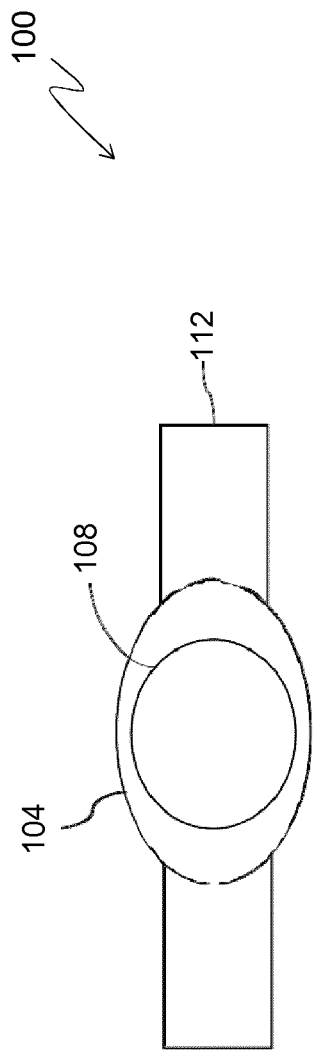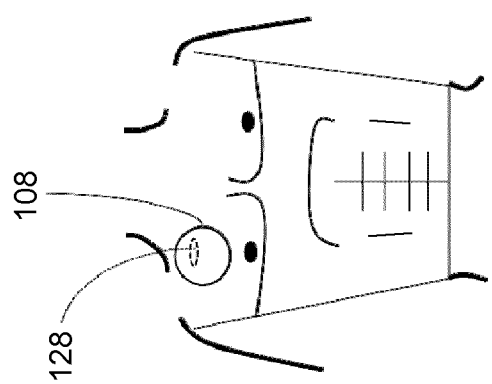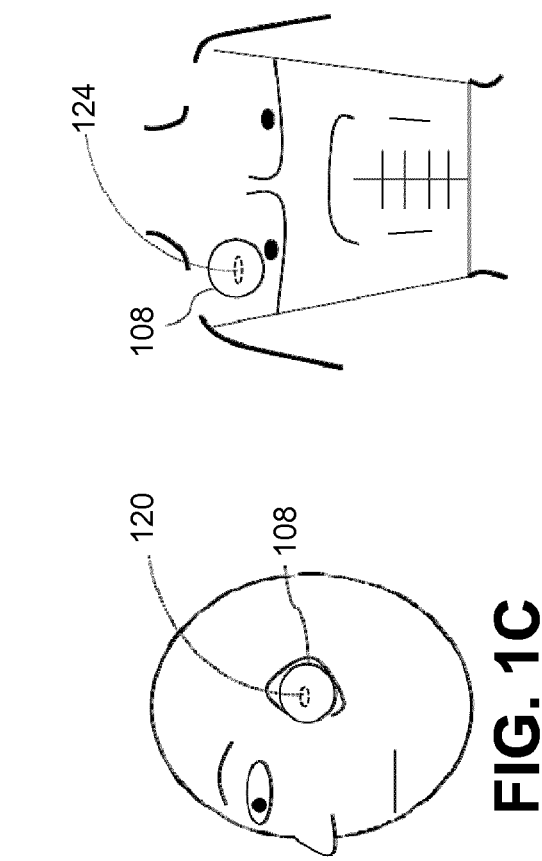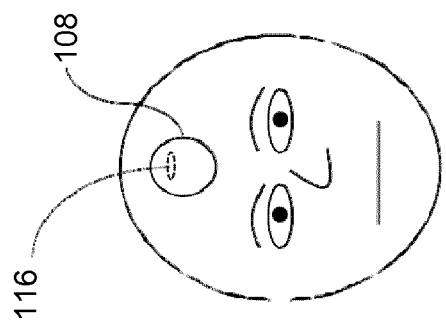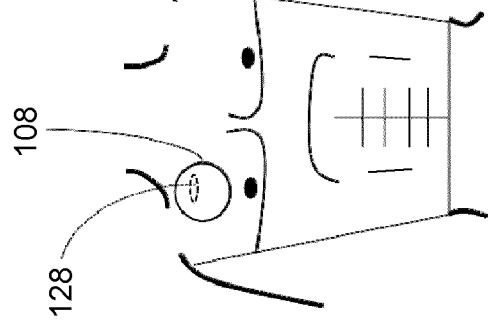

| DATE | TIME | PULSE | HRT SND | SWT ALS | FRHD T | OP EAR T | LNG SND |
|---|---|---|---|---|---|---|---|
| 12/1/14 | 9:20AM | -- | HeartSound1.wav | -- | -- | -- | -- |
| 12/1/14 | 9:23AM | 117 | | -- | -- | -- | -- |
| 12/1/14 | 9:26AM | -- | -- | -- | 102.4 | -- | -- |
| 12/1/14 | 9:29AM | -- | -- | -- | -- | 102.3 | -- |
| 12/1/14 | 9:32AM | -- | -- | Electrolytes normal | -- | -- | -- |
| 12/1/14 | 9:35AM | -- | -- | -- | -- | -- | LungSound1.wav |

| DATE | TIME | PULS | TEMP | RESP RATE |
|---|---|---|---|---|
| 12/1/14 | 9:00A | 85 | 98 | 12/MIN |
| 12/1/14 | 9:05A | 81 | 99 | 15/MIN |
| 12/1/14 | 9:10A | 90 | 99 | 14/MIN |
| 12/1/14 | 9:15A | 120 | 102 | 25/MIN |

| Parameter | Reading | Required Action |
|---|---|---|
| Pulse | 85 | No |
| Pulse | 100 | No |
| Pulse | 120 | Place on Chest to measure Pulse and record Heart Beat |
| ••• | ••• | ••• |
| Temperature | 98 | No |
| Temperature | 100 | Place on Forehead for Sweat and Temp. Reading, Place over Ear for Temp. Reading |
| Temperature | 102 | Place on Forehead for Sweat and Temp. Reading, Place over Ear for Temp. Reading |
| ••• | ••• | ••• |
| Respiratory Rate | 12/Min | No |
| Respiratory Rate | 17/Min | No |
| Respiratory Rate | 23/Min | Place on Chest to Measure Lungs |
| ••• | ••• | ••• |

| MANUAL SENSOR READING | REQUIRED ACTION |
|---|---|
| EAR TEMPERATURE | PLACE OVER EAR FOR TEMP READING |
| FOREHEAD TEMP/SWEAT | PLACE ON FOREHEAD FOR SWEAT AND TEMP. READING |
| LUNG SOUNDS | PLACE ON CHEST TO RECORD LUNG SOUNDS |
| HEART BEAT SOUND/PULSE | PLACE ON CHEST TO MEASURE PULSE AND RECORD HEART SOUNDS |

FIG. 5

WEARABLE AND DETACHABLE HEALTH PARAMETER SENSOR

CROSS REFERENCE TO RELATED APPLICATION

This application claims the priority benefit under 35 U.S.C. § 371 of International Patent Application No. PCT/EP2016/054949, filed Mar. 9, 2016, which claims the benefit of priority of U.S. Provisional Patent Application Ser. No. 62/130,134, filed on Mar. 9, 2015, entitled "WEARABLE TECHNOLOGY DEVICE HAVING A DETACHABLE HEALTH PARAMETER SENSOR APPARATUS AND METHODS AND SOFTWARE FOR SAME," and which claims the benefit of European Application No. EP15177049.2 filed Jul. 16, 2015, which are hereby incorporated by reference herein in their entirety.

FIELD OF THE INVENTION

The present invention generally relates to the field of wearable health monitoring.

BACKGROUND OF THE INVENTION

Some current-generation wearable technology devices, such as smartwatches, fitness bands, and health wearables, include one or more sensors for measuring various conditions or states of the wearer. Such sensors include pulse sensors for measuring the wearer's pulse, temperature sensors for measuring the wearer's temperature, and accelerometers for measuring the wearer's movement. Depending on the type of wearable device and how it is worn, in some cases the sensor(s) are not always located on the wearer in a location for optimizing the measurements and in other cases the wearing location is simply not suitable for taking measurements of certain health parameters. Consequently, designers of current-generation wearable technology devices must make compromises in the functionality, robustness, and convenience of their devices. For instance, in WO 2014/028736, entitled, "Obtaining Physiological Measurements Using a Portable Device," a portable, handheld device is disclosed that comprises two optical sensors located on a planar surface at a fixed distance from each other. When measurements are desired, the user positions the planar surface on the wrist, and blood flow measurements are obtained.

SUMMARY OF THE INVENTION

One object of the present invention is that a wearable device can automatically and repeatedly monitor health parameters of a user to provide sensor data and responsive to an out-of-range value corresponding to the sensor data, instruct the user to locate sensors of the wearable device to another location.

To better address such concerns, in a first aspect of the invention, a system (200) comprising a wearable base (104) and a detachable health-parameter sensor apparatus (108) detachably coupled to the base, the detachable health-parameter sensor apparatus automatically and repeatedly monitoring one or more health parameters of a user, and responsive to determining a need for truer readings, instructing the user to locate the health-parameter sensor apparatus to another location on the user. The present invention addresses a problem in the art where current health monitoring devices inconveniently require user intervention and lack flexibility in monitoring by using wearable sensors for automatic and repeated monitoring of health parameters, where the sensors are detachable to enable truer readings when instructed to do so based on out-of-limit conditions.

In one embodiment, the system instructs, via a user interface, the user to deploy the detachable health parameter sensor apparatus from the base to a location relative to a body part of the user for a measurement collection mission, sense, by the one or more sensors, the one or more health parameters to generate the sensor data, collect, via the base, the sensor data while the detachable health parameter sensor apparatus is deployed at the location, and notify the user that the measurement collection mission has ended. The ability to re-locate the sensors to obtain a truer reading and feed the sensor data to the base while deployed at the different location provides for both truer readings while also providing up-to-date readings.

In one embodiment, the system measures a value of the sensor data, compares the value to a corresponding parameter limit, and when the value is outside the corresponding parameter limit, triggers the instructing. The use of limits enables the automatic and repeated monitoring until it is determined that truer readings may be available.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. In certain instances, details that are not necessary for an understanding of the embodiments or that render other details difficult to perceive may have been omitted. Moreover, in the drawings, like reference numerals designate corresponding parts throughout the several views.

FIG. 1A is a schematic diagram that illustrates in top view an example wearable technology device having a detachable health parameter sensor apparatus, wherein the device is embodied in a form for wearing on a user's wrist, in accordance with an embodiment of the invention.

FIG. 1B is a schematic diagram that illustrates in partial frontal view the detachable health parameter sensor apparatus applied to the user's forehead for forehead-based body temperature sensing, in accordance with an embodiment of the invention.

FIG. 1C is a schematic diagram that illustrates in partial side view the detachable health parameter sensor apparatus applied over the user's ear for ear-based body temperature sensing, in accordance with an embodiment of the invention.

FIG. 1D is a schematic diagram that illustrates in partial frontal view the detachable health parameter sensor apparatus applied to the user's upper chest away from the heart for sensing lung sounds from breathing, in accordance with an embodiment of the invention.

FIG. 1E is a schematic diagram that illustrates in partial frontal view the detachable health parameter sensor apparatus applied to the user's upper chest proximate to the heart for sensing heart sounds, in accordance with an embodiment of the invention.

FIG. 4 is a schematic diagram that illustrates an example limits database that can be implemented in connection with a wearable technology device, in accordance with an embodiment of the invention.

FIG. 5 is a schematic diagram that illustrates an example manual reading database that can be implemented in connection with a wearable technology device, in accordance with an embodiment of the invention.

DETAILED DESCRIPTION OF EMBODIMENTS

Figure 2:
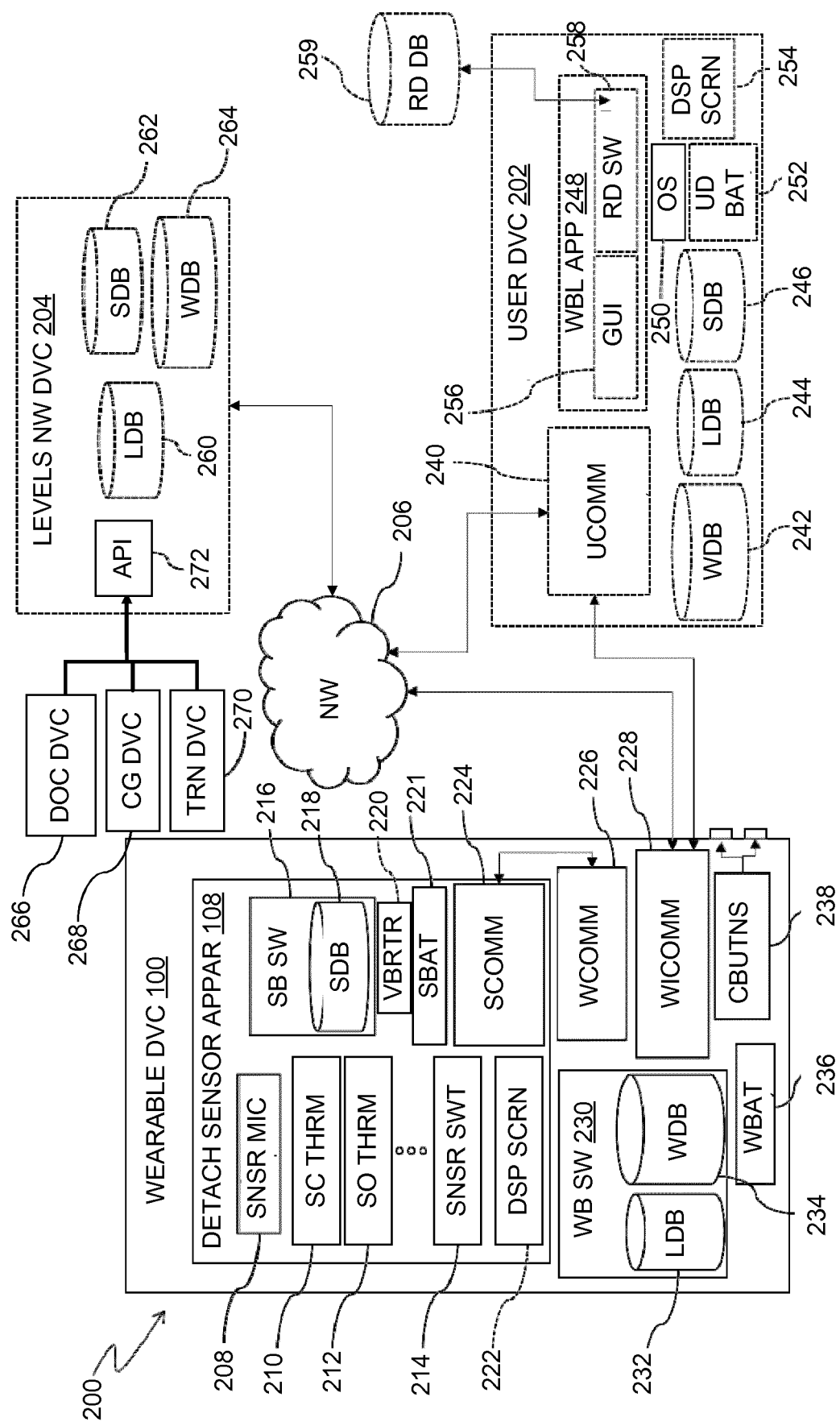
FIG. 2 is a schematic diagram that illustrates an example health parameter monitoring system that includes a wearable technology device having a detachable health parameter sensor apparatus, in accordance with an embodiment of the invention.

Aspects of the present invention are directed to a wearable technology device, such as a smartwatch, fitness-band, health-band, smartglasses, or other software-driven wearable device, having a detachable health parameter sensor apparatus that can be removably detached from a base of the wearable device. The detachable health parameter sensor apparatus can be configured to automatically and repeatedly measure any one or more of a variety of measurable health parameters of a human wearer (hereinafter, "user"), such as vital signs (e.g., temperature, pulse, respiratory rate, blood pressure), heart sounds, heartbeat, lung breathing sounds, perspiration, blood sugar level, among others. As will be understood from reading this entire disclosure, such a wearable technology device enables a variety of functionalities heretofore unknown in the realm of health and body status monitoring. For example, the present inventors have found that conventional wearable technology devices have sensors, such as temperature and pulse sensors, that can sense health parameters, but the sensor(s) is/are not necessarily in the optimal location for the truest reading. As an example, a smartwatch having a temperature sensor can measure body temperature, but only at the user's wrist, which does not yield a true reading of core temperature, which is critical to health monitoring. Consequently, one new functionality is that a user can detach the detachable health parameter sensor apparatus from the wearable technology device and move it to a location where truer readings can be obtained. For example, a user can detach and move a detachable health parameter sensor apparatus having a temperature sensor to the user's forehead or other location that provides a truer measure of core temperature. This can, in some embodiments, be coupled with routine monitoring in which the detachable health parameter sensor apparatus remains attached to the base, but wherein the wearable technology device can notify the user that a truer reading is needed and instruct the user to detach the detachable health parameter sensor apparatus and place it at a certain location for taking the truer reading.

As another example, another new functionality is that routine monitoring of one or more health parameters at a wearing location of the wearable technology device may reveal that the user is experiencing a certain abnormal health condition but that additional health parameter data for one or more other health parameters not able to be sensed at the wearing location is needed to make a determination with higher certainty. In this case, the user can deploy the detachable health parameter sensor apparatus to a location relative to the user's body where it can be used to collect health parameter data for the additional health parameter(s). Those skilled in the art will readily appreciate that these are only a few introductory examples. Further examples are illustrated below in more detail.

In some aspects, the present disclosure is directed to a wearable technology device having a base and a detachable health parameter sensor apparatus that removably engages the base so that the user can de-dock the detachable health parameter sensor apparatus from the base for deployment to a particular location relative to the users body. This detachability/re-attachability allows, for example, a user to acquire health parameter data that is of a better quality or for a health parameter that cannot be measured from the normal wearing location of the wearable technology device. As described below in detail, these and other aspects of the present disclosure allow for robust health monitoring and related novel methods and software.

Turning now to the drawings, FIG. 1A illustrates a wearable technology device 100 made in accordance with the present invention. In the embodiment shown, the wearable technology device (also referred to herein simply as "wearable device") is in the form of a wrist-worn device that may be similar to a smartwatch, though it should be appreciated by one having ordinary skill in the art that the wearable technology device 100 may be located elsewhere on the body (or garments covering a location of the body) in some embodiments. Here, wearable device 100 includes a base 104, a detachable health parameter sensor apparatus 108, and a securing device for securing the wearable device to a user (not shown). In FIG. 1A, detachable health parameter sensor apparatus 108 is shown docked with base 104, and the securing device is a wristband 112. A number of things are noted relative to wearable device 100 of FIG. 1A. For example, the shapes and sizes of detachable health parameter sensor apparatus 108 may be different from the shapes and sizes shown, and the shapes and sizes may be dictated by any suitable criteria, including type of device (e.g., watch type, arm-band type, chest-band type, etc.), sensor size and/or configuration constraints, and/or constraints of other components, such as processors, communications systems, memory, displays, etc., that provide wearable device 100 with its desired functionality, among others. As another example and as noted above, a wearable device in accordance with the present invention need not necessarily be worn directly on the body or body part. Consequently, the securing device can be any suitable device, such as a clamp, strap, glove, headgear, hat, footwear, body protector, compression garment, etc., that allows a user to wear the wearable device directly on a body part and/or by way of an article of clothing, clothing accessory, hat, headgear, footwear, glove, body protector, etc., that the user is wearing and can hold a portion of the wearable device in contact with the wearer for repeated and automatic monitoring of one or more physiological parameters. Fundamentally, there is no limit on the manner in which a wearable device of the present invention can be worn by a user. In addition, it is noted that wearable device 100 can include any functionality other than the functionality particularly addressed by this disclosure, such as time-keeping functionality, communications functionality (e.g., cell phone), general purpose computing functionality, altimeter functionality, and barometric pressure functionality, among others, and any combination thereof. Similarly, there is fundamentally no limitation to the other types of functionality that can be included in a wearable device of the present invention.

FIGS. 1B to 1E illustrate example, but by no means exclusive, scenarios that require a user to detach detachable health parameter sensor apparatus 108 from base 104 of wearable device 100 and place it at particular locations on or proximate to the body. As will be understood from reading this entire disclosure, the user may place detachable health parameter sensor apparatus 108 at the corresponding location, for example, in response to being prompted to do so, such as by wearable device 100 or another device (e.g., a user device, such as a smartphone, tablet computer, etc.), either automatically based on prior monitoring data or in response to the user desiring to take a manual reading, among others. For the examples of FIGS. 1B to 1E, it is noted that only detachable health parameter sensor apparatus 108 is shown; the base of the wearable device remains secured to the user in its original location, here, on the wrist (not shown) of the user.

FIG. 1B illustrates a scenario in which detachable health parameter sensor apparatus 108 includes a contact-type temperature sensor 116 and it is desired to obtain a truer reading of the user's body temperature by contacting detachable health parameter sensor apparatus 108 with the user's forehead. As an example of this scenario, temperature readings automatically (e.g., without user intervention) and repeatedly (e.g., periodically, aperiodically, etc.) taken at the user's wrist when detachable health parameter sensor apparatus 108 is docked with base 104 of wearable device 100 may have revealed that it was advisable to get a truer reading using forehead temperature. In this example, wearable device 100 (FIG. 1A) and/or a user device (not shown) may have prompted the user to deploy detachable health parameter sensor apparatus 108 to her/his forehead. Relatedly, FIG. 1C illustrates a similar body temperature scenario. However, the difference is that the temperature sensor on detachable health parameter sensor apparatus 108 is an ear-type temperature sensor 120, and the user has either been instructed to move detachable health parameter sensor apparatus 108 over one of her/his ears or has moved the detachable sensor to the required location without prompting.

FIG. 1D illustrates a scenario in which detachable health parameter sensor apparatus 108 includes a sensor 124, such as a microphone, for sensing lung activity. As an example of this scenario, pulse readings taken at the user's wrist when detachable health parameter sensor apparatus 108 is docked with base 104 of wearable device 100 may have revealed that it was advisable to obtain lung activity data. In this example, wearable device 100 (FIG. 1A) and/or a user device (not shown) may have prompted the user to deploy detachable health parameter sensor apparatus 108 to her/his upper chest, at a location away from the heart to minimize interference of heart activity with lung activity.

FIG. 1E illustrates a scenario in which detachable health parameter sensor apparatus 108 includes a sensor 128, such as a microphone, for sensing heart activity. As an example of this scenario, pulse readings taken at the user's wrist when detachable health parameter sensor apparatus 108 is docked with base 104 of wearable device 100 may have revealed that it was advisable to obtain additional heart activity data. In this example, wearable device 100 (FIG. 1A) and/or a user device (not shown) may have prompted the user to deploy (e.g., relocate) detachable health parameter sensor apparatus 108 to her/his upper chest proximate to the heart to maximize the quality of the heart related data.

FIG. 2 illustrates an example health-parameter monitoring system 200 made in accordance with the present invention. In this particular embodiment, health parameter monitoring system 200 includes wearable device (WEARABLE DVC) 100, an optional user device (USER DVC) 202, and an optional levels network device (LEVELS NW DVC) 204 that may communicate directly with one another and/or via one or more communications networks (NW) 206, including the cloud and/or Internet 206. Wearable device 100 includes detachable health parameter sensor apparatus (DETACH SENSOR APPAR) 108 having a variety of components that provide it with its requisite functionality and allow it to function when deployed remotely from base 104 of wearable device 100 (FIG. 1). In one embodiment, the base 104 and the health parameter sensor apparatus 108 each have their own respective processor. In some embodiments, the wearable device 100, the user device 202, and the levels network device (also, herein network device) 204 each have one or more processors disposed therein. In the example shown, these components include one or more sensors 208-214, memory containing sensor base software (SB SW) 216 and one or more sensor databases (SDB) 218, a power source (here, a battery, SBAT) 221, a sensor communications system (SCOMM) 224, an optional vibrator (VBRTR) 220 (or other haptic device), and an optional display screen (DSP SCRN) 222. Example sensors that can be included in detachable health parameter sensor apparatus 108 include a microphone (SNSR MIC) 208, a contact thermometer (SC THERM) 210, an optical thermometer (SO THERM) 212, and a sweat sensor (SNSR SWT) 214, among others. The sensor base software 216 allows base 104 and detachable health parameter sensor apparatus 108 to work together and the detachable health parameter sensor apparatus to execute its functionalities. The sensor database 218 can store sensor data from the two or more sensors 208-214 onboard detachable health parameter sensor apparatus 108. The optional vibrator 220, or other haptic device, can be used to signal the user that certain events have occurred, such as a reading has been obtained or the user needs to reposition detachable health parameter sensor apparatus 108, among others. The optional display screen 222 can be the sole or primary display screen of the overall wearable device 100, or it can be an auxiliary or sister display screen to a display screen (not illustrated) on the base. Sensor communications system 224 enables detachable health parameter sensor apparatus 108 to communicate with base 104 via a corresponding wearable communications system (WCOMM) 226 onboard base 104 of wearable device 100. In some embodiments, the sensor and wearable communications systems, 224 & 226, respectively, may be in communication via hardwiring, such as using a micro USB connector that allows communications between detachable health parameter sensor apparatus 108 and base 104 only when the detachable health parameter sensor apparatus is docked with the base. In other embodiments, communications between the sensor and wearable communications systems, 224 & 226, respectively, may be achieved wirelessly to allow communications between the two components when detachable health parameter sensor apparatus 108 is remotely deployed relative to base 104. In some embodiments, the sensor and wearable communications systems 224 & 226 may be configured for functioning using both wired and wireless communications functionality.

In this example, base 104 of wearable device 100 includes in addition to wearable communications system 226 that communicates with detachable health parameter sensor apparatus 108, other components that provide base 104 with various functionalities, such as a wireless communications system (WICOMM) 228, memory containing wearable base software (WB SW) 230 and wearable device (WD)—limits and wearable device—wearable databases (LDB) 232 & (WDB) 234, respectively, a power source, here a battery (WBAT) 236, and a user interface, here, control buttons (CBUTNS) 238. Wireless communications system 228 allows wearable device 100 to communicate directly with user device 202 and/or with other devices via the network 206. Wireless communications system 228 may include any one or more types of wireless transceivers, including but not limited to, WI-FI™ and BLUETOOTH™ transceivers, among others. Wearable base software 230 allows base 104 and detachable health parameter sensor apparatus 108 to work together and base 104 to execute its functionalities, including communicating with user device 202 and other devices via network 206. Wearable device wearable database 234 can store sensor data from sensors 208-214 onboard detachable health parameter sensor apparatus 108 when the detachable health parameter sensor apparatus is docked with base 104, and wearable device limits database 232 may contain various limits for health parameter readings that wearable device 100 can use to determine whether or not it should prompt a user to deploy detachable health parameter sensor apparatus 108 to obtain one or more additional health-parameter readings. The user interface may be used to allow a user to interact with wearable device 100, including controlling various functionalities relating to health-parameter readings and deployment of detachable health parameter sensor apparatus 108. It is noted that base 104 may include other features, such as one or more displays, which may provide one or more user interfaces, and one or more haptic devices, which may provide one or more types of alerts to the user, among others.

User device 202, if present, may be a smartphone or other suitable device. The embodiment of the health-parameter monitoring system 200 as shown includes user device 202, which can perform the support/enable functions to wearable device 100 in a manner similar to the way that smartphones support current smartwatches. In some embodiments, the user device 202 may be omitted, with functionality of the user device 202 illustrated herein incorporated directly into wearable device 100.

In this example, user device 202 includes a wireless user device communications system (UCOMM) 240, user device (UD) databases 242 (WDB), 244 (LDB), 246 (SDB), a wearable software application ("wearable app 248" or WBL APP), a user-device operating system (OS) 250, a power source, here a battery 252 (UD BAT), and one or more display screens (DSP SCRN) 254. Wireless user device communications system 240 allows user device 202 to communicate directly with wearable device 100 and with other devices via the network 206. Wireless user device communications system 240 may include any one or more types of wireless transceivers, including but not limited to, WI-FI™ and BLUETOOTH™ transceivers, among others. In this example, the user device databases include a user device wearable database (WDB) 242, a user device limits database (LDB) 244, and a user device sensor database (SDB) 246. User device wearable database 242 contains sensor data acquired by detachable health parameter sensor apparatus 108 while the detachable health parameter sensor apparatus is docked with base 104, such as wrist pulse data when wearable device 100 is a wrist-worn device. User device sensor database 246 contains sensor data acquired by detachable health parameter sensor apparatus 108 when the detachable health parameter sensor apparatus is deployed remotely from base 104 of wearable device 100. User device limits database 244 may contain various limits for health parameter readings that wearable device 100 can use to determine whether or not it should prompt a user to deploy detachable health parameter sensor apparatus 108 to obtain one or more additional health-parameter readings.

Wearable app 248 in this example provides a wearable app graphical user interface (GUI) 256 that allows a user to interact with wearable app 248 and control various functionality of wearable device 100. This example of wearable app 248 also includes manual reading software (RD SW) 258 that allows a user to acquire health-parameter readings outside any automated prompting that takes place using the limits in user device limits database 244. Any readings taken using manual reading software 258 may be stored in a manual reading database (RD DB) 259. These features are described in more detail below. User device OS 250 is the operating system that controls the overall operation of user device 202. Examples include the iOS operating system available from Apple, Inc., the Android OS available from Google, Inc., Windows Phone OS available from Microsoft, Inc., and the BlackBerry OS available from BlackBerry Limited. Each user device display screen 254 may be embodied as any suitable display device technology, typically, but not exclusively, a touch-type screen or similar display device technology.

Levels network device 204 in this example comprises a number of databases (260, 262, 264) and an application programming interface (API) 272. Here, the example databases include a levels network (LN)-limits database (LDB) 260, and levels network sensor database (SDN) 262, and levels network wearable database (WDB) 264. As described below, levels network limits database 260 includes limits to which actual readings are compared and that are used to trigger user action to seek additional readings using detachable health parameter sensor apparatus 108. Levels network limits database 260 may be populated by health care professionals, such as doctors via doctors device (DOC DVC) 266 and caregivers via caregivers device (CG DVC) 268, and by others, such as trainers via trainers device (TRN DVC) 270. API 272 is configured to allow these people or their agents to populate levels network limits database 260. The limits in levels network limits database 260 may be generic for all users of a multi-user system, or may be specific, for example, specially created for each specific user or class of users, such as classification by age, by fitness level, by health malady(ies), health history, etc. Levels network wearable database 264 contains sensor data acquired from one or more wearable devices 100 of one or more corresponding users when detachable health parameter sensor apparatus 108 is docked with base 104. Levels network sensor database 262 contains sensor data acquired from one or more wearable devices 100 of one or more corresponding users when detachable health parameter sensor apparatus 108 is deployed remotely from base 104 of wearable device 100.

As one example of how health-parameter monitoring system 200 can work, wearable device 100 may automatically take some base readings repeatedly (e.g., periodically, for example, every five minutes) and write the sensor readings to wearable device wearable database 234. These sensor readings are compared with limits (e.g., ranges, max/min values, etc.) in wearable device limits database 232 to make sure that they are within the limits. If they are, then wearable device 100 just keeps automatically and repeatedly taking these readings. If they are not within the limits and there is a required action determined from wearable device limits database 232, then the user is prompted to detach detachable health parameter sensor apparatus 108 to take a more accurate reading on a different part of their body.

For example, it could be the sensed user temperature was deemed outside of the limit, so wearable device 100 prompts the user to detach detachable health parameter sensor apparatus 108 and to place it on their forehead. Then the sensor base software takes a temperature reading from their forehead (FIG. 1B), writes the value of the temperature reading into wearable device sensor database 218, and vibrates via vibrator 220, to let the user know that it is done taking the reading. In some embodiments, the user may be alerted according to other mechanisms, including lighting on the wearable device, sound (e.g., via speaker), etc. The user then reattaches detachable health parameter sensor apparatus 108 to base 104 of wearable device 100, at which time communications may be reconnected between the detachable health parameter sensor apparatus and the base of the wearable device if the communications is hardwired.

Once detachable health parameter sensor apparatus 108 is docked, the updated wearable device wearable database 234 data and updated wearable device sensor database 218 data may then be communicated to both user device 202 and levels network device 204 and that data is then available in the respective sensor databases and wearable databases, which then allows the user, through their user device 202, to look at the different readings using wearable app 248. The user may also, with wearable app 248, prompt a manual reading through wearable app GUI 256, and manual reading software 258 may prompt the user again to detach detachable health parameter sensor apparatus 108 and take the manually-prompted sensor reading. For example, if the original reading was a forehead temperature (FIG. 1B) and the user wants another temperature reading but this time over the ear (FIG. 1C), the user detaches detachable health parameter sensor apparatus 108, places it over the ear and the detachable health parameter sensor apparatus takes the reading and writes it to wearable device sensor database 218 and vibrates via vibrator 220 to let the user know the reading is done. At that point, the user may reattach detachable health parameter sensor apparatus 108 to base 104 of wearable device 100, and then the updated wearable device sensor database 218 data is sent to user device 202 for storage in manual reading database 259, copied to user device sensor database 246, and then user device 202 may then send that data to levels network 204 through the network 206.

Figures 3A, 3B:
FIG. 3A is a schematic diagram that illustrates an example database containing data from a detachable health parameter sensor apparatus when the detachable apparatus is deployed remotely from a base of the wearable technology device, in accordance with an embodiment of the invention.
FIG. 3B is a schematic diagram that illustrates an example database containing data from the detachable health parameter sensor apparatus when the detachable apparatus is docked with the base of the wearable technology device, in accordance with an embodiment of the invention.

FIG. 3A illustrates a data table 300 showing example contents of each of the wearable device sensor 218, user device sensor 246, and levels network sensor 262 databases after all have been populated with the same data. As noted above, sensor databases 218, 246, 262 contain data from detachable health parameter sensor apparatus 108 when it is deployed remotely from base 104 of wearable device 100. As seen here, sensor databases 218, 246, 262 are populated with data of differing types taken at differing times and at differing locations on the user's body. For instance, the column headings indicate possible readings associated with pulse, heart sound (HRT SND), sweat analysis (SWT ALS), forehead temperature (FRHD T), optical ear temperature (OP EAR T), and lung sounds (LNG SND) in this example.

FIG. 3B illustrates a data table 304 showing example contents of each of wearable device wearable 234, user device wearable 242, and levels network wearable 264 databases after all have been populated with the same data. As noted above, wearable databases 234, 242, 264 contain data from detachable health parameter sensor apparatus 108 when it is docked with base 104 of wearable device 100. As seen here, wearable databases 234, 242, 264 are populated with data of three differing types (e.g., pulse, temperature (TEMP), respiration rate (RESP RATE)), wherein all three readings are taken simultaneously and periodically. It should be apparent from the above description that various ones of these values can be compared to corresponding limits in limits databases 232, 244, 260 to trigger prompting a user to take an action to acquire one or more additional readings by deploying detachable health parameter sensor apparatus 108 remotely from base of wearable device 100.

FIG. 4 illustrates a data table 400 showing example contents of each of wearable device limits 232, user device limits 244, and levels network limits 260 databases after all have been populated with the same data. As noted above and described below, the information in limits databases 232, 244, 260 is used to make determinations of whether or not the user should be prompted, for example, via wearable device 100 and/or user device 202, to take one or more additional readings by deploying detachable health parameter sensor apparatus 108 remotely from base 104 of wearable device 202. The decision-making can be accomplished by repeatedly comparing readings in one or more of wearable databases 234, 242, 264 (i.e., readings taken while detachable health parameter sensor apparatus 108 is docked with base 104 of wearable device 100) to the reading data in one or more of the limits databases 232, 244, 260 to see if a limit is reached. If so, the relevant device, for example, wearable device 100 and/or user device 202, can prompt the user to take the additional action(s).

FIG. 5 illustrates a data table 500 showing an example of the manual reading database 259 mentioned above in connection with the user device of FIG. 2. This database may contain required action information to be displayed to a user when the user desires to manually take a certain type of reading. Wearable app 248 onboard user device 202 can control, in conjunction with the information in manual reading database 259, the user interface (see below) that the user interacts with to acquire manual readings with detachable health parameter sensor apparatus 108.

Figure 6:
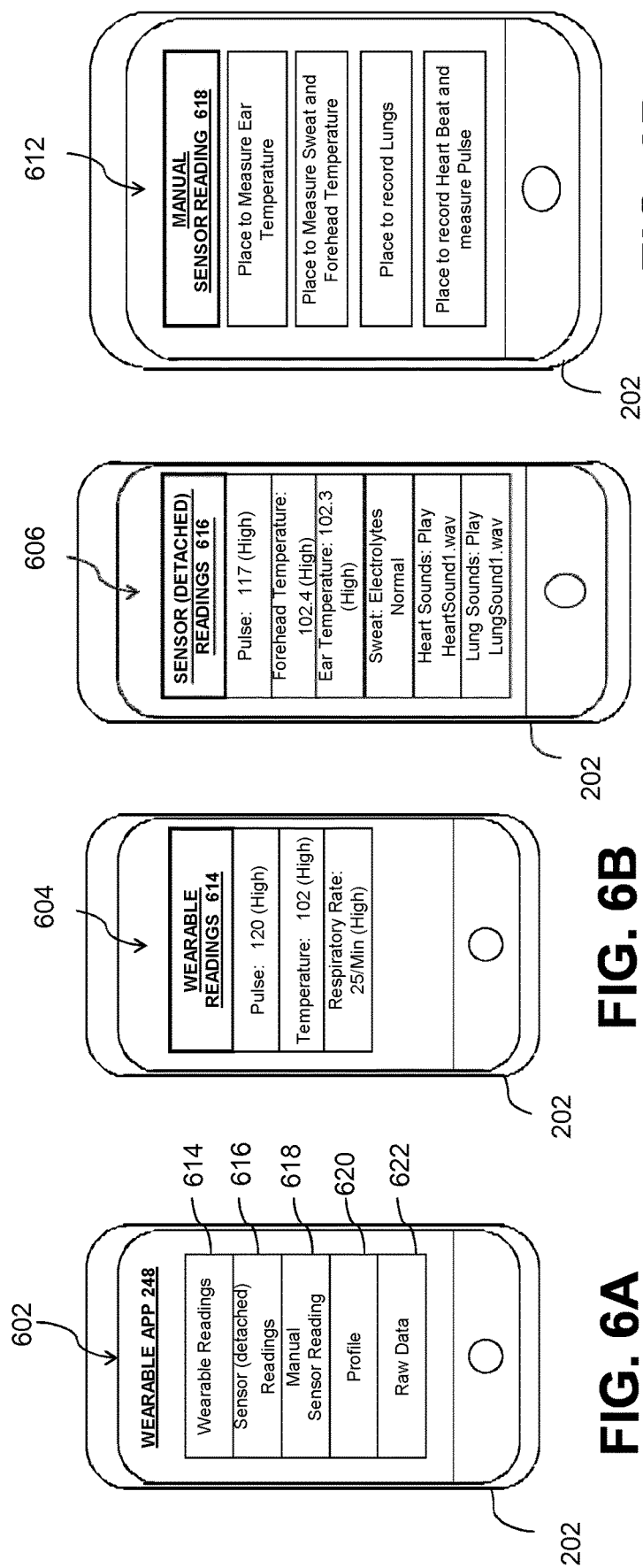
FIG. 6A is a schematic diagram that illustrates a front view of a user device running a wearable application (also referred to herein as "wearable app"), illustrating an example home screen of the wearable app, in accordance with an embodiment of the invention.
FIG. 6B is a schematic diagram that illustrates a front view of a user device running the wearable app of FIG. 6A, illustrating an example wearable readings screen, in accordance with an embodiment of the invention.
FIG. 6C is a schematic diagram that illustrates a front view of a user device running the wearable app of FIG. 6A, illustrating an example sensor (detached) readings screen, in accordance with an embodiment of the invention.
FIG. 6D is a schematic diagram that illustrates a front view of a user device running the wearable app of FIG. 6A, illustrating an example manual sensor reading screen, in accordance with an embodiment of the invention.

FIGS. 6A to 6D illustrate example GUI screens 602, 604, 606, 612 that wearable app 248 aboard user device 202 of FIG. 2 can display to a user. FIG. 6A illustrates user device 202 displaying a home screen 602 of the wearable app 248. Screen 604 gives a user five options: 1) to display the wearable (docked) readings (614) (see FIG. 6B); 2) to display the sensor (detached) readings (616) (see FIG. 6C); 3) to display manual sensor reading instructions (618) (see FIG. 6D); 4) to display/edit the user's profile (620); and 5) to display raw data (622). Those skilled in the art will understand that the screens shown are merely example and that many variations and alternatives are possible. In some embodiments, the GUI screens 602, 604, 606, and/or 612 may be presented on wearable device 100.

Figure 7:
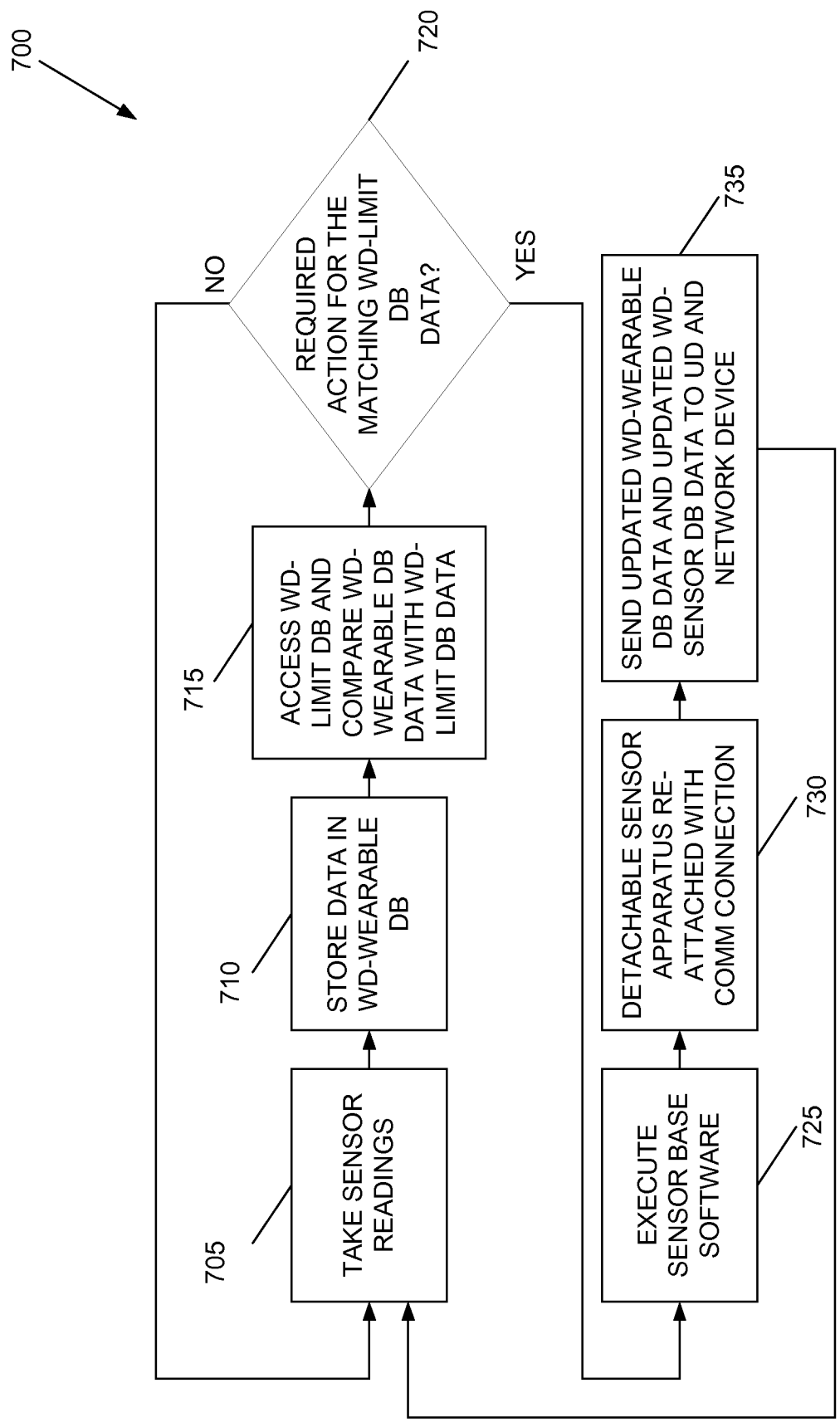
FIG. 7 is a flow diagram that illustrates an example health parameter monitoring method that can be executed by software running on a base of a wearable technology device having a detachable health parameter sensor apparatus, in accordance with an embodiment of the invention.
Figure 8:
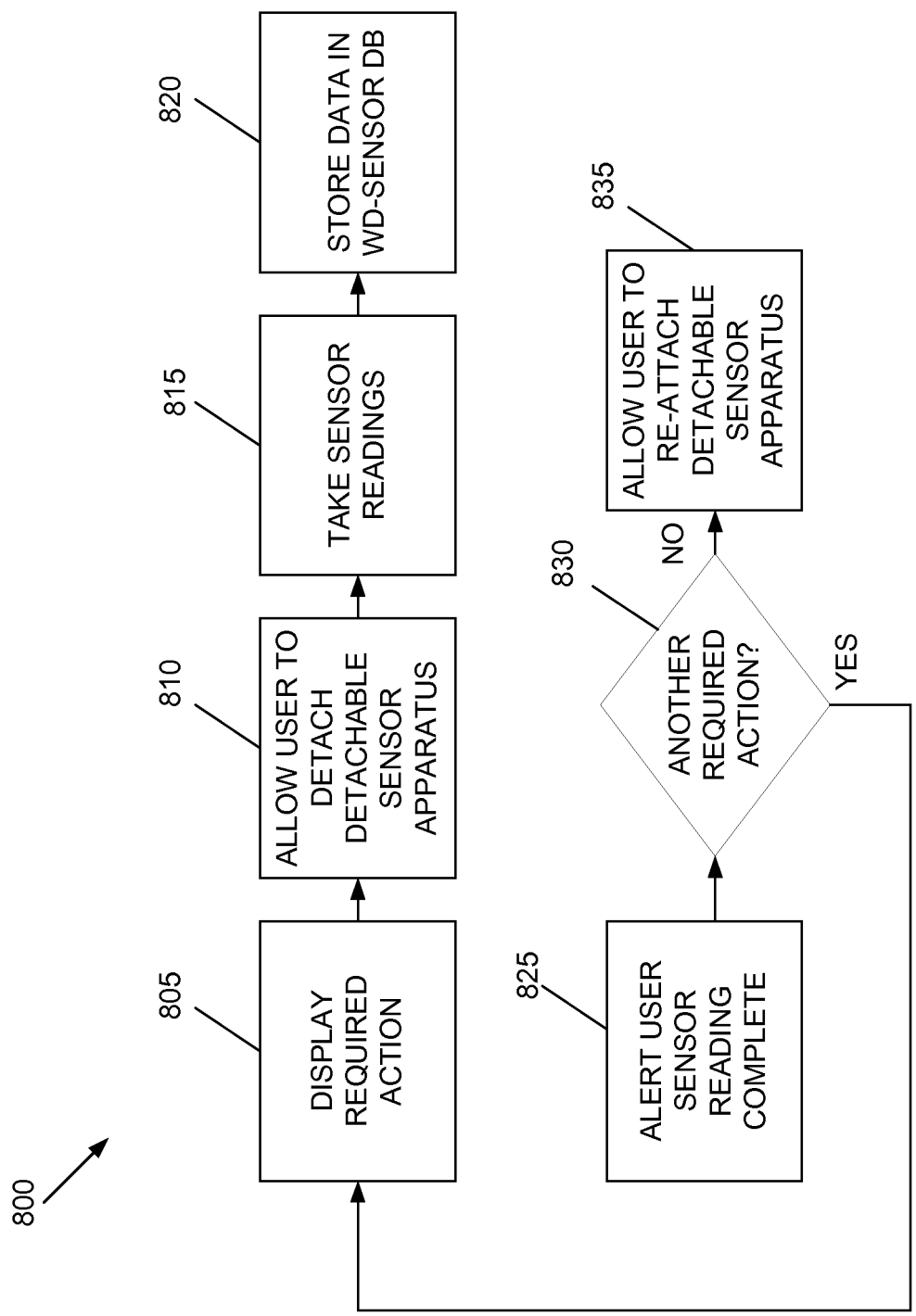
FIG. 8 is a flow diagram that illustrates an example detachable health parameter sensor apparatus deployment method that can be executed by software running on a base of a wearable technology device having a detachable health parameter sensor apparatus, in accordance with an embodiment of the invention.

FIG. 7 illustrates an example method 700 that can be executed by wearable base software 230 of wearable device 100 to periodically take readings (here, every five minutes) at step 705 with detachable health parameter sensor apparatus 108 docked with base 104 of wearable device 100, at step 710 storing those readings in wearable device wearable database 234 at step 715, and comparing those readings to corresponding limits in wearable device limits database 232. If there is no match (720), then the periodic reading continues. However, if there is a match, then at step 725 the method 800 of FIG. 8 is executed, after which method 700 of FIG. 7 continues as shown at steps 700 through 735. As shown in step 725, the sensor base software is executed. In step 730, the detachable sensor apparatus has been reattached to the wearable device via connection between the sensor COMM (e.g., hardwired, including by micro USB) to the wearable COMM (e.g., hardwired, including by micro USB). In step 735, the updated wearable device, wearable device database data is sent to the user device and network device wearable databases, and the updated wearable device sensor database data is sent to the user device and network device wearable sensor databases via the wearable communications (e.g., Bluetooth, WiFi, etc.).

FIG. 8 illustrates method 800 that can be executed by sensor base software 216 of detachable health parameter sensor apparatus 108 upon matching of at least one limit based on the readings in wearable device wearable database 234. Once sensor base software 216 has executed method 800 of FIG. 8, wearable base software 230 of base 104 of wearable device 100 may continue executing method 700 of FIG. 7 at steps 730 and 735. Described above. The flow diagram of FIG. 8 comprises a display of required action on wearable display in step 805, allow user to detach the detachable sensor apparatus, which disconnects the sensor COMM—hardwired (e.g. micro-USB), and to place it on the prompted body part in step 810. In step 815, sensor readings are taken, and step 820 comprises storing data in wearable device sensor database. Step 825 comprises alerting user (e.g., vibrate, visual alert, audible alert, etc.) to notify user that the sensor reading is complete, and step 830 comprises a decision whereby if there is no other action required, allow user to reattach the detachable sensor apparatus to the wearable device, which connects the sensor COMM—hardwired (e.g., micro-USB) to the wearable COMM—hardwired (e.g., micro-USB) in step 835, otherwise (if yes to step 825) return to step 805.

Figure 9:
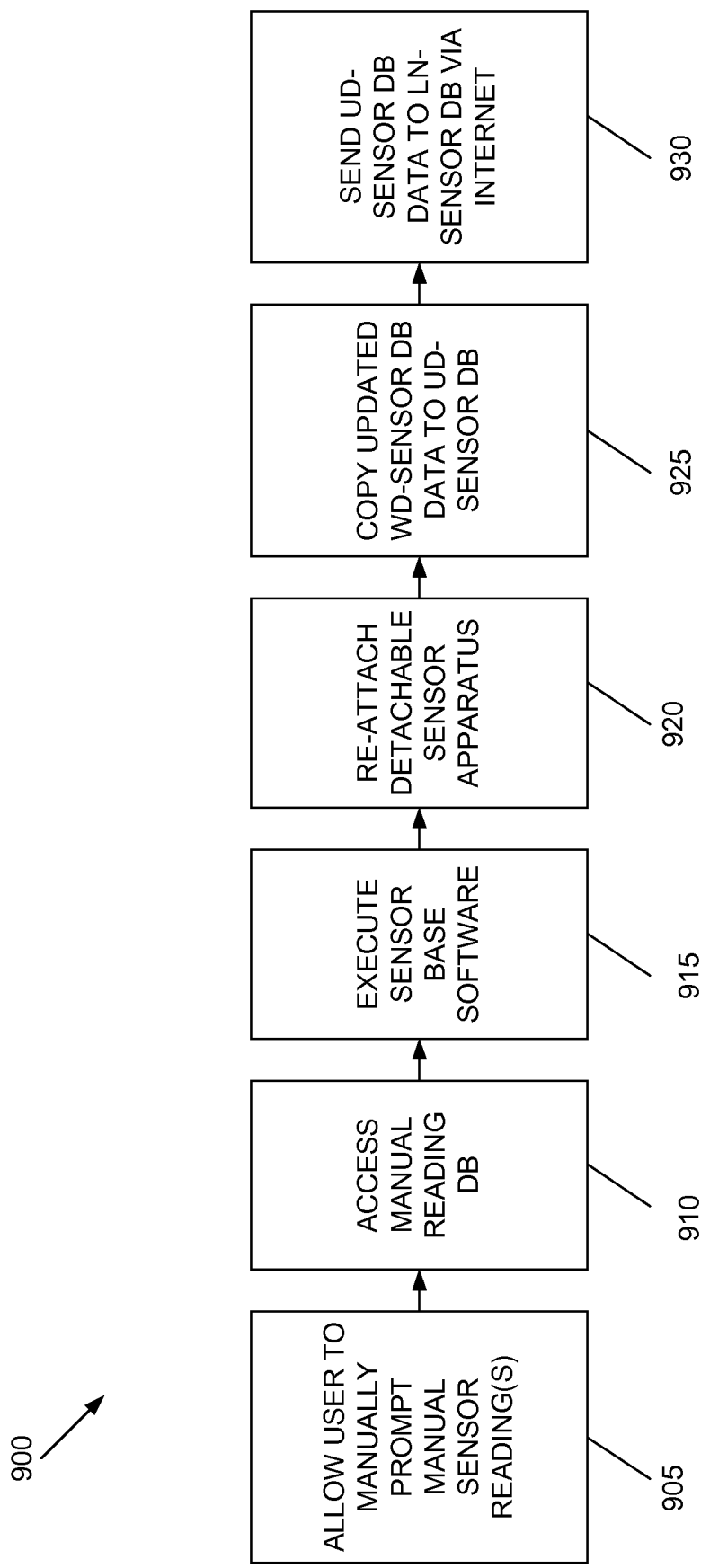
FIG. 9 is a flow diagram that illustrates an example manual reading method that can be executed by software running on a base of a wearable technology device having a detachable health parameter sensor apparatus, in accordance with an embodiment of the invention.

FIG. 9 illustrates an example method 900 that can be used to allow a user to obtain manual readings by deploying detachable health parameter sensor apparatus 108 from the wearable device 100. The first two steps can be executed by wearable app 248 on user device 202. The third step can include executing method 800 of FIG. 8, and the remaining steps involve communicating the obtained reading(s) and storing the readings to sensor databases. As depicted in FIG. 9, the method 900 comprises allowing user to manually prompt one or multiple manual sensor readings using the wearable app GUI (905), accessing manual reading database to determine required action(s) for chosen manual sensor reading(s) (910), executing sensor base software (915), reattaching detachable sensor apparatus to the wearable device, which has connected the sensor COMM—hardwired (e.g., micro-USB) to the wearable COMM—hardwired (e.g., micro-USB) (920), copy updated wearable device sensor database data to user device sensor database via communication between wearable communications (e.g., Bluetooth or WiFi) and the user device communication (e.g., Bluetooth or WiFi) (925), and send user device sensor database data to network device sensor database via the internet (930).

Figure 10:
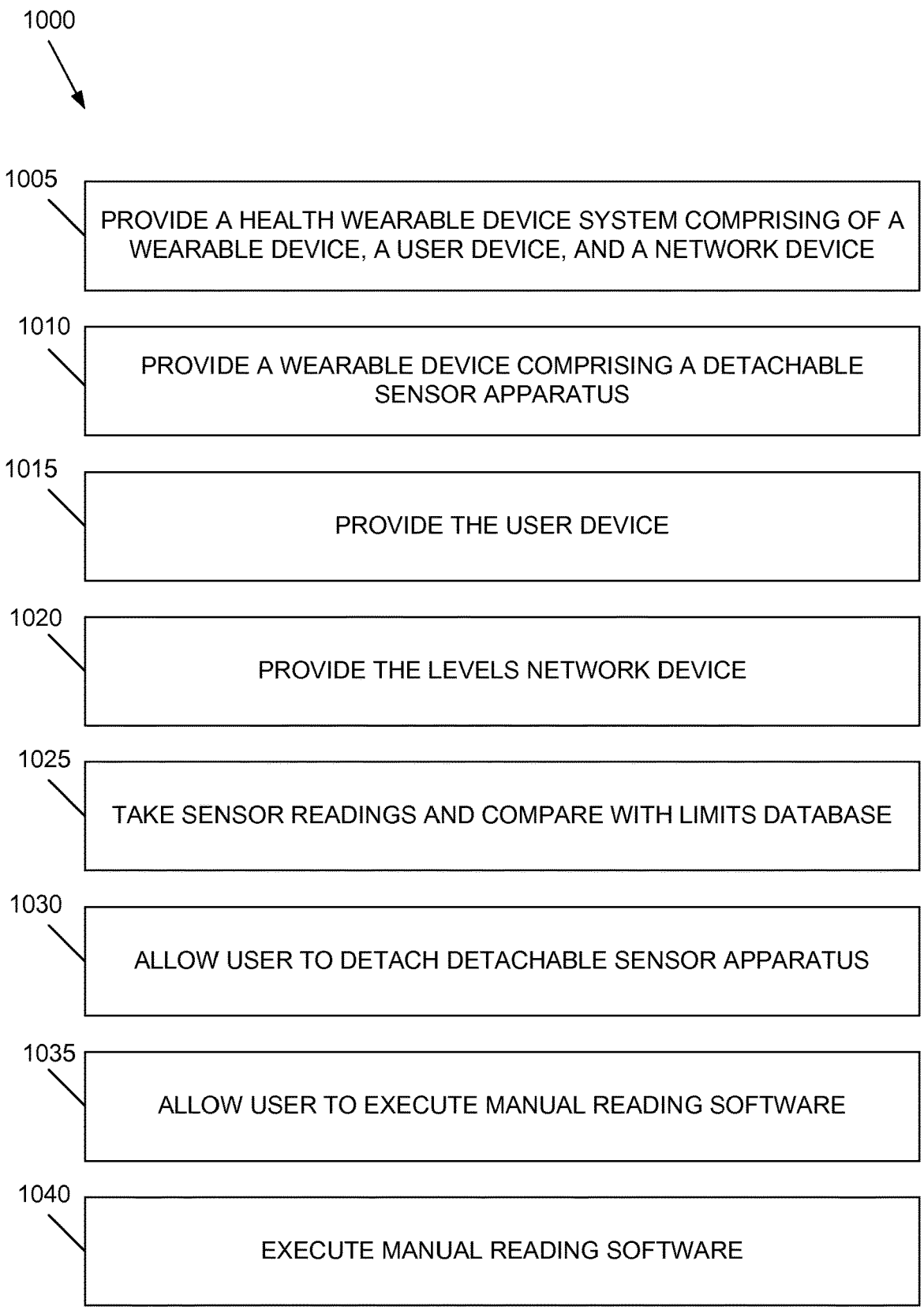
FIG. 10 is a flow diagram that illustrates an example overall method that incorporates use of a wearable technology device having a detachable health parameter sensor apparatus, in accordance with an embodiment of the invention.

FIG. 10 illustrates an overall method 1000 of utilizing health-parameter monitoring system 200 of FIG. 2. As seen, the steps of the method of FIG. 10 are quite self-explanatory when read in the context of the health-parameter monitoring system of FIG. 2. Those skilled in the art will readily appreciate that the method of FIG. 10 is merely one example, and many other methods that include subsets of the steps of this method may be devised in accordance with changes to and/or alternative uses of health-parameter monitoring system 200 of FIG. 2. The method 1000 comprises providing a health wearable device system comprising of a wearable device, a user device, both of which are connected through the internet or the cloud to a levels network device (1005), providing the wearable device comprising a wearable COMM—hardwired (e.g. micro-USB), a wearable communications (e.g., Bluetooth or WiFi), control buttons, a wearable battery, a wearable base software which further comprises a wearable device—limits database and a wearable device—wearable database, and a detachable sensor apparatus which further comprises a plurality of sensors, a wearable display screen, a vibrator, a sensor battery, a sensor COMM—hardwired (e.g. micro-USB), and a sensor base software further comprising a wearable device—sensor database (1010), providing the user device comprising a user device communications (e.g. Bluetooth or WiFi), a user device—wearable database, a user device—limits database, a user device—sensor database, an OS, a user device battery, a user device display screen, and a wearable app which further comprises a wearable app GUI and a manual reading software (1015), providing a levels network device comprising a levels network device—limits database, a levels network device—sensor database, a levels network device—wearable database, and an API allowing doctors, caregivers, and trainers access to the levels network device (1020), executing the wearable base software to take sensor readings (e.g., every 5 minutes) to store data in the wearable device—wearable database, to access the wearable device—limit database and compare the wearable device—wearable database data with the wearable device—limit database data, to decide if there is a required action for the matching wearable device—limit database data, if no to return to taking sensor readings (e.g., every 5 minutes), if yes to execute sensor base software, and once the detachable sensor apparatus has been reattached to the wearable device to send the updated wearable device—wearable database data and wearable device—sensor database data to the user device and levels network device using the wearables communications (e.g., Bluetooth or WiFi) (1025), executing the sensor base software to display the required action on the wearable display screen, to allow the user to detach the detachable sensor apparatus and place it on the prompted body part, to take sensor readings, to store data in the wearable device—sensor database, to alert (e.g., vibrate) to notify the user that the sensor reading is complete, to decide if there is another required action, if yes to display the required action on the wearable display screen and start the process over, if no to allow the user to reattach the detachable sensor apparatus to the wearable device (1030), allowing the user to execute the manual reading software (1035), executing the manual reading software to allow the user to manually prompt one or multiple manual sensor readings using the wearable app GUI, to access the manual reading database to determine the required action(s) for the chosen manual sensor reading(s), to execute the sensor base software, and once the detachable sensor apparatus has been reattached to the wearable device to copy the updated wearable device—sensor database data to the user device—sensor database via communication between the wearable communications (e.g. Bluetooth or WiFi) and the user device communications (e.g., Bluetooth or WiFi), and to send the user device—sensor database data to the levels network device—sensor database via the Internet (1040).

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
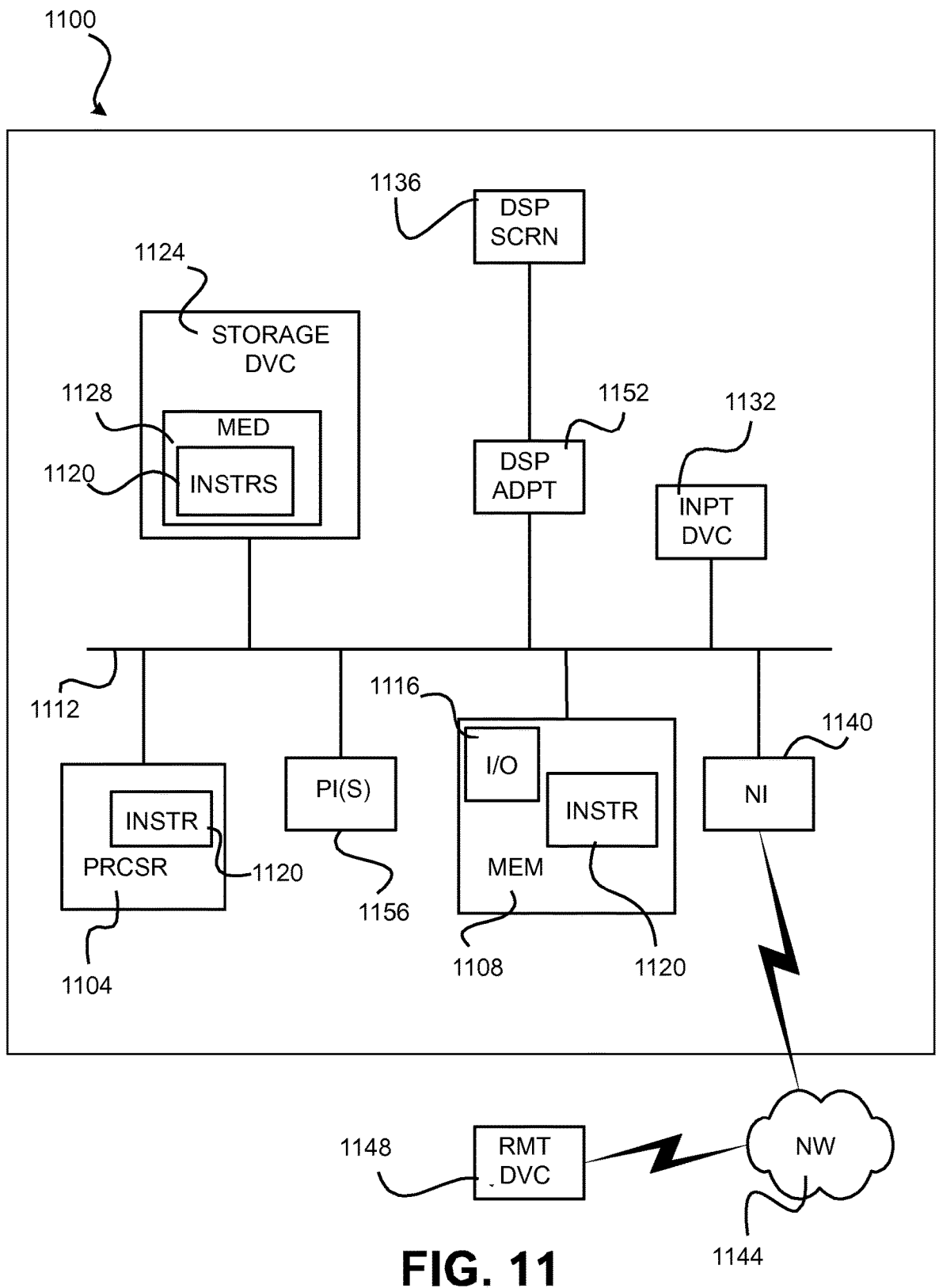
FIG. 11 is a high-level schematic diagram of a computing system that can be used to implement any one or more of the methodologies of the present disclosure, in accordance with an embodiment of the invention.

FIG. 11 shows a diagrammatic representation of one embodiment of a computing device in the example form of a computer system 1100 within which a set of instructions for causing a control system, such as any one or more of various systems of the present disclosure, such as the systems illustrated in other figures of this disclosure, as well as systems that would be apparent to those of ordinary skill in the art after reading this entire disclosure, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor (PRCSR) 1104 and a memory (MEM) 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Memory 1108 may include various components (e.g., machine-readable media) including, but not limited to, a random access memory component, a read only component, and any combinations thereof. In one example, a basic input/output system (I/O) 1116 (BIOS), including basic routines that help to transfer information between elements within computer system 1100, such as during start-up, may be stored in memory 1108. Memory 1108 may also include (e.g., stored on one or more machine-readable media) instructions (INSTRS) (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device (STORAGE DVC) 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium (MED) 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device (INPT DVC) 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIREWIRE interface, a direct interface to bus 1112, and any combinations thereof. Input device 1132 may include a touch screen interface that may be a part of or separate from display screen (DSP SCRN) 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device (NI) 1140. A network interface device, such as network interface device 1140, may be utilized for connecting computer system 1100 to one or more of a variety of networks, such as network (NW) 1144, and one or more remote devices (RMT DVC) 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter (DSP ADPT) 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface (PI) 1156. Examples of a peripheral interface include, but are not limited to, a serial port, a USB connection, a FIREWIRE connection, a parallel connection, and any combinations thereof.

In one embodiment, a first independent claim is disclosed and directed to a system comprising: a wearable base comprising a first communication system; a health parameter sensor apparatus detachably coupled to, and in communication with, the base, the health parameter sensor apparatus comprising a second communication system in communication with the first communication system and one or more sensors, the one or more sensors configured to automatically and repeatedly monitor one or more health parameters of a user and provide sensor data; a user interface; and a processor configured to receive the sensor data, and responsive to the sensor data corresponding to an out-of-range health parameter, instructing via the user interface that the user detach the health parameter sensor apparatus and locate it elsewhere on the user to obtain a truer reading. The system of the first independent claim, wherein the first communication system further comprises a physical communications connector having mating components, wherein the first and second communication systems include corresponding respective ones of the mating components. The system of the first independent claim, wherein the processor is further configured to: instruct, via the user interface, the user to deploy the detachable health parameter sensor apparatus from the base to a location relative to a body part of the user for a measurement collection mission; sense, by the one or more sensors, the one or more health parameters to generate the sensor data; collect, via the base, the sensor data while the detachable health parameter sensor apparatus is deployed at the location; and notify the user that the measurement collection mission has ended. The system of the prior claim, wherein the processor is further configured to: measure a value of the sensor data; compare the value to a corresponding parameter limit; and when the value is outside the corresponding parameter limit, triggering the instructing. The system of the prior claim, wherein the first communication system is configured to wirelessly transmit the sensor data from the detachable health parameter sensor apparatus to the base. The system of the first independent claim, wherein the processor is further configured to: instruct, via the user interface, the user to deploy the detachable health parameter sensor apparatus from the base to a location relative to a body part of the user for a measurement collection mission; sense, by the one or more sensors, the one or more health parameters to generate the sensor data; notify the user that the measurement collection mission has ended; and transmit via the first and second communication systems the sensor data corresponding to the sensed one or more health parameters via a hardwired connection when the detachable health parameter sensor apparatus is physically attached to the base after the measurement collection mission. The system of the prior claim, wherein the processor is further configured to: measure a value of the sensor data; compare the value to a corresponding parameter limit; and when the value is outside the corresponding parameter limit, triggering the instructing.

The system of the first independent claim, wherein the processor is disposed in the base, wherein the base comprises a third communication system configured to transmit the sensor data to another device. The system of the first independent claim, wherein the processor is disposed in a user device, wherein the sensor data is received from the base according to a third communication system. The system of the first independent claim, wherein the processor is disposed in a network device, the sensor data received over a network.

In one embodiment, a second independent claim is disclosed and directed to a machine-readable storage medium containing machine-executable instructions to cause one or more processors to: automatically and repeatedly receive sensor data corresponding to one or more health parameters monitored by one or more sensors of a health parameter sensor apparatus detachably coupled to a base secured to a user; and responsive to the sensor data corresponding to an out-of-range health parameter, cause presentation of user instructions that the user detach the health parameter sensor apparatus and locate it elsewhere on the user to obtain a truer reading. The machine-readable storage medium of the second independent claim, wherein the machine-executable instructions further cause the one or more processors to: present user instructions to the user, the user instructions instructing the user to deploy the detachable health parameter sensor apparatus from the base to a location relative to a body part of the user for a measurement collection mission; wirelessly collect the sensor data while the detachable health parameter sensor apparatus is deployed at the location; and notify the user that the measurement collection mission has ended. The machine-readable storage medium of the prior claim, wherein the machine-executable instructions further cause the one or more processors to: measure a value of the one or more sensor data; compare the value to a corresponding parameter limit; and when the value is outside the corresponding parameter limit, triggering the presentation of the user instructions. The machine-readable storage medium of the second independent claim, wherein the machine-executable instructions further cause the one or more processors to: present the user instructions to the user, the user instructions instructing the user to deploy the detachable health parameter sensor apparatus from the base to a location relative to a body part of the user for a measurement collection mission; notify the user that the measurement collection mission has ended; and receive the sensor data corresponding to the sensed one or more health parameters via a hardwired connection when the detachable health parameter sensor apparatus is physically attached to the base after the measurement collection mission. The machine-readable storage medium of the prior claim, wherein the machine-executable instructions further cause the one or more processors to: measure a value of the one or more sensor data; compare the value to a corresponding parameter limit; and when the value is outside the corresponding parameter limit, triggering the presentation of the user instructions. The machine-readable storage medium of the second independent claim, wherein the one or more processors are disposed in the base, wherein the machine-executable instructions further cause the one or more processors to transmit the sensor data to another device. The machine-readable storage medium of the second independent claim, wherein the one or more processors are disposed in a user device. The machine-readable storage medium of the second independent claim, wherein the one or more processors are disposed in a network device.

In one embodiment, a third independent claim is disclosed and directed to a method, comprising: automatically and repeatedly receiving sensor data corresponding to one or more health parameters monitored by one or more sensors of a health parameter sensor apparatus detachably coupled to a base secured to a user; and responsive to the sensor data corresponding to an out-of-range health parameter, causing presentation of instructions that the user detach the health parameter sensor apparatus and locate it elsewhere on the user to obtain a truer reading. The method of the third independent claim, wherein the method is implemented in any one or a combination of a wearable device, a user device wirelessly coupled to the base, or a network device coupled to the user device.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve various aspects of the present disclosure. Accordingly, this description is meant to be taken only by way of example, and not to otherwise limit the scope of this invention.

Example embodiments have been disclosed above and illustrated in the accompanying drawings. It will be understood by those skilled in the art that various changes, omissions and additions may be made to that which is specifically disclosed herein without departing from the spirit and scope of the present invention.

At least the following is claimed:

1. A system, comprising:
   a wearable base that comprises a first communication system;
   a health parameter sensor apparatus detachably coupled to, and in communication with, the wearable base, wherein the health parameter sensor apparatus comprises a second communication system in communication with the first communication system and one or more sensors, the one or more sensors configured to automatically and repeatedly monitor one or more health parameters of a user and provide first sensor data while the health parameter sensor apparatus is docked to the wearable base;
   a user interface; and
   a processor configured to receive the first sensor data, and responsive to the first sensor data corresponding to an out-of-range health parameter, instructing via the user interface that the user detach the health parameter sensor apparatus from the wearable base and locate the health parameter sensor apparatus elsewhere on the user to obtain a truer reading of second sensor data, wherein responsive to the health parameter sensor apparatus being both (i) detached from the wearable base and (ii) located elsewhere on the user, the processor obtains the truer reading of second sensor data.

2. The system of claim 1, wherein the first communication system further comprises a physical communications connector having mating components, wherein the first and second communication systems include corresponding respective ones of the mating components.

3. The system of claim 1, wherein the processor is configured to determine the first sensor data corresponds to an out-of-range health parameter by comparing at least one value of the first sensor data to a corresponding parameter limit,
wherein responsive to the at least one value being outside the corresponding parameter limit, the processor triggers the instructing.

4. The system of claim 1, wherein the processor is disposed in the wearable base, wherein the wearable base comprises a third communication system configured to transmit the first sensor data or the second sensor data to another device.

5. The system of claim 1, wherein the processor is disposed in a user device, wherein the first sensor data or the second sensor data is received from the wearable base according to a third communication system.

6. The system of claim 1, wherein the processor is disposed in a network device, wherein the first sensor data or the second sensor data is received from the wearable base over a network.

7. A system comprising:
a wearable base that comprises a first communication system;
a health parameter sensor apparatus detachably coupled to, and in communication with, the wearable base, wherein the health parameter sensor apparatus comprises a second communication system in communication with the first communication system and one or more sensors, the one or more sensors configured to automatically and repeatedly monitor one or more health parameters of a user and provide first sensor data while the health parameter sensor apparatus is docked to the wearable base;
a user interface; and
a processor configured to receive the first sensor data, and responsive to the first sensor data corresponding to an out-of-range health parameter, instructing via the user interface that the user detach the health parameter sensor apparatus and locate it elsewhere on the user to obtain a truer reading, wherein the processor is configured to perform the instructing by causing presentation of instructions to the user to deploy the health parameter sensor apparatus from the wearable base to a location relative to a body part of the user for a measurement collection mission, wherein the processor is further configured to, while the health parameter sensor apparatus is detached from the wearable base:
wirelessly receive, via a communication system, from the one or more sensors, second sensor data corresponding to a truer reading of the one or more monitored health parameters,
wherein the health parameter sensor apparatus is further configured to notify the user when the measurement collection mission has ended.

8. A system comprising:
a wearable base that comprises a first communication system;
a health parameter sensor apparatus detachably coupled to, and in communication with, the wearable base, wherein the health parameter sensor apparatus comprises a second communication system in communication with the first communication system and one or more sensors, the one or more sensors configured to automatically and repeatedly monitor one or more health parameters of a user and provide first sensor data while the health parameter sensor apparatus is docked to the wearable base;
a user interface; and
a processor configured to receive the first sensor data, and responsive to the first sensor data corresponding to an out-of-range health parameter, instructing via the user interface that the user detach the health parameter sensor apparatus and locate it elsewhere on the user to obtain a truer reading, wherein the second communication system is configured to wirelessly transmit second sensor data corresponding to a truer reading of the one or more monitored health parameters from the health parameter sensor apparatus to the wearable base while the health parameter sensor apparatus is detached from the wearable base.

9. A system comprising:
a wearable base that comprises a first communication system;
a health parameter sensor apparatus detachably coupled to, and in communication with, the base, wherein the health parameter sensor apparatus comprises a second communication system in communication with the first communication system and one or more sensors, the one or more sensors configured to automatically and repeatedly monitor one or more health parameters of a user and provide first sensor data while the health parameter sensor apparatus is docked to the wearable base;
a user interface; and
a processor configured to receive the first sensor data, and responsive to the first sensor data corresponding to an out-of-range health parameter, instructing via the user interface that the user detach the health parameter sensor apparatus and locate it elsewhere on the user to obtain a truer reading, wherein the processor is configured to perform the instructing:
by causing presentation of instructions to the user to deploy the health parameter sensor apparatus from the wearable base to a location relative to a body part of the user for a measurement collection mission, wherein the health parameter sensor apparatus is configured to notify the user when the measurement collection mission has ended,
wherein the processor is further configured to, upon detecting that the health parameter sensor apparatus is re-attached to the wearable base, receive from the one or more sensors over a hardwired connection between the wearable base and the health parameter sensor apparatus, second sensor data corresponding to a truer reading of the one or more health parameters monitored by the one or more sensors when the health parameter sensor apparatus was detached from the wearable base.

10. A non-transitory machine-readable storage medium containing machine-executable instructions to cause one or more processors to:
automatically and repeatedly receive first sensor data corresponding to one or more health parameters monitored by one or more sensors of a health parameter sensor apparatus detachably coupled to a wearable base secured to a user;
compare respective values of the first sensor data to corresponding parameter limits;
responsive to at least one of the values of the first sensor data being outside the corresponding parameter limit, cause presentation of user instructions, the user instructions instructing the user to deploy the health parameter sensor apparatus from the wearable base to a location relative to a body part of the user for a measurement collection mission; and receive second sensor data from the health parameter sensor apparatus subsequent to the presentation of the user instructions, in response to the health parameter sensor apparatus being detached from the wearable base and located at the location relative to the body part of the user for the measurement collection mission, the second sensor data corresponding to a truer reading of the one or more health parameters monitored by the one or more sensors.

11. The non-transitory machine-readable storage medium of claim 10, wherein the one or more processors are disposed in the wearable base, wherein the machine-executable instructions further cause the one or more processors to transmit the sensor data to another device.

12. The non-transitory machine-readable storage medium of claim 10, wherein the one or more processors are disposed in a user device.

13. The non-transitory machine-readable storage medium of claim 10, wherein the one or more processors are disposed in a network device.

14. A non-transitory machine-readable storage medium containing machine-executable instructions to cause one or more processors to:
automatically and repeatedly receive first sensor data corresponding to one or more health parameters monitored by one or more sensors of a health parameter sensor apparatus detachably coupled to a wearable base secured to a user;
compare respective values of the first sensor data to corresponding parameter limits;
responsive to at least one of the values of the first sensor data being outside the corresponding parameter limit, cause presentation of user instructions, the user instructions instructing the user to deploy the health parameter sensor apparatus from the wearable base to a location relative to a body part of the user for a measurement collection mission; and
subsequent to the presentation of the user instructions, wirelessly receive second sensor data, via a communication system, from the health parameter sensor apparatus while the health parameter sensor apparatus is deployed at the location, the second sensor data corresponding to a truer reading of the one or more health parameters monitored by the one or more sensors.

15. A non-transitory machine-readable storage medium containing machine-executable instructions to cause one or more processors to:
automatically and repeatedly receive first sensor data corresponding to one or more health parameters monitored by one or more sensors of a health parameter sensor apparatus detachably coupled to a wearable base secured to a user;
compare respective values of the first sensor data to corresponding parameter limits;
responsive to at least one of the values of the first sensor data being outside the corresponding parameter limit, cause presentation of user instructions, the user instructions instructing the user to deploy the health parameter sensor apparatus from the wearable base to a location relative to a body part of the user for a measurement collection mission; and
subsequent to the presentation of the user instructions, receive second sensor data from the health parameter sensor apparatus via a hardwired connection based on detecting that the health parameter sensor apparatus is physically attached to the wearable base after the measurement collection mission, the second sensor data corresponding to a truer reading of the one or more health parameters monitored by the one or more sensors.

16. A method, comprising:
automatically and repeatedly receiving first sensor data corresponding to one or more health parameters monitored by one or more sensors of a health parameter sensor apparatus detachably coupled to a wearable base secured to a user;
comparing respective values of the first sensor data to corresponding parameter limits;
responsive to at least one of the values of the first sensor data being outside the corresponding parameter limit, causing presentation of user instructions, the user instructions instructing the user to deploy the health parameter sensor apparatus from the wearable base to a location relative to a body part of the user for a measurement collection mission; and
receiving second sensor data from the health parameter sensor apparatus subsequent to the presentation of the user instructions to the user, in response to the health parameter sensor apparatus being deployed from the wearable base and located at the location relative to the body part of the user for the measurement collection mission, the second sensor data corresponding to a truer reading of the one or more health parameters monitored by the one or more sensors.

17. The method of claim 16, wherein the method is implemented in any one or a combination of a wearable device, a user device wirelessly coupled to the wearable base, or a network device coupled to the user device.

* * * * *